United States Patent [19]

Kawata et al.

[11] 4,394,383

[45] Jul. 19, 1983

[54] N-ALKOXYSULFENYLCARBAMATES USEFUL AS INSECTICIDES

[75] Inventors: Mitsuyasu Kawata; Noriharu Umetsu; Tetsuo R. Fukuto, all of Riverside, Calif.

[73] Assignee: Regents of the University of California, Berkeley, Calif.

[21] Appl. No.: 306,437

[22] Filed: Sep. 28, 1981

[51] Int. Cl.³ ................... A01N 47/24; C07D 307/86; C07C 161/00
[52] U.S. Cl. ..................................... 424/285; 424/275; 424/278; 424/282; 424/277; 424/283; 424/300; 549/21; 549/23; 549/33; 549/51; 549/362; 549/399; 549/438; 549/470; 260/464; 260/465 D; 260/465.4; 560/10; 560/12; 560/13; 560/134; 560/135; 560/136; 560/137; 560/148
[58] Field of Search ................. 260/340.5 R, 340.9 R, 260/346.73, 347.2, 465 D, 465.4, 464; 549/51, 21, 23, 33, 362, 399, 470; 560/12, 13, 10, 115, 134, 135, 136, 137, 148; 424/275, 278, 282, 285, 299, 300, 277, 283

[56] References Cited

U.S. PATENT DOCUMENTS

| | | | |
|---|---|---|---|
| 3,843,689 | 10/1974 | Brown | 260/346.73 |
| 3,997,549 | 12/1976 | Fukuto et al. | 424/285 |
| 4,006,231 | 2/1977 | Black et al. | 424/248.5 |
| 4,261,897 | 4/1981 | Fahmy et al. | 260/465 D |
| 4,262,015 | 4/1981 | Fahmy et al. | 424/282 |
| 4,263,318 | 4/1981 | Fahmy et al. | 424/282 |
| 4,298,617 | 11/1981 | Fahmy et al. | 424/298 |
| 4,308,274 | 12/1981 | Fahmy et al. | 424/267 |

OTHER PUBLICATIONS

Karchmer, Chem. Analysis-The Analytical Chem. of Sulfur and Its Compounds-Part I-Wiley, (1970), p. 434.
Reid, Organic Chem. of Bivalent Sulfur-vol. I, Chem. Publishing Co., (1958), p. 126.

*Primary Examiner*—John M. Ford
*Assistant Examiner*—Bernard Dentz
*Attorney, Agent, or Firm*—Nilsson, Robbins, Dalgarn, Berliner, Carson & Wurst

[57] ABSTRACT

A novel class of chemical compounds useful as pesticides consists of N-alkoxysulfenylcarbamate esters. The preparation of these compounds, their physical properties, formulations, and use to control both household insects and crop pests are exemplified.

9 Claims, No Drawings

N-ALKOXYSULFENYLCARBAMATES USEFUL AS INSECTICIDES

FIELD OF THE INVENTION

This invention relates to the general field of pesticides, and is particularly concerned with the production of insecticides for the control of both household insects and crop insects.

BACKGROUND AND SUMMARY OF THE INVENTION

Various types of carbamate pesticides have been previously described. For example, U.S. Pat. No. 3,997,549 to Fukuto and Black discloses N-arylsulfenylated derivatives of benzofuranyl methylcarbamates as effective pesticides; U.S. Pat. No. 4,006,231 to Black and Fukuto discloses N-aminosulfenylated derivatives of carbofuran as effective pesticides; and U.S. Pat. No. 3,843,689 to Brown et al. discloses the production of N-methyl-N-phenyldithiocarbamate from the N-chlorothiocarbamates (i.e. N-chlorosulfenylcarbamate).

Further with regard to the last-mentioned patent, Brown et al. refer in rather broad-brush fashion to the reaction of N-chlorosulfenylcarbamates with a wide variety of substituents, including alcohols, mercaptans, ureas, carbamates, amines, amides, anilides, and other compounds that have active hydrogen atoms to give the corresponding substitution product and hydrochloric acid by reaction with the sulfenyl halide component of the compound. Brown et al. do not appear to have actually performed some of the reactions, for example, with alcohol, inasmuch as details of processing to yield a useful product are not given.

In accordance with the present invention, a novel class of carbamate ester compounds are provided, which are effective pesticides. The carbamate compounds are derived in accordance with one of several reaction routes, one of which involves the reaction of an N-chlorosulfenylcarbamate ester. However, in contrast with the simple chemistry envisioned by the Brown et al. U.S. Pat. No. 3,843,689, we have discovered that a sulfur-polymerizing reaction occurs when pyridine or other suitable base is used as a hydrogen chloride acceptor. We have further found that in order to prepare the resultant alkoxy compound substantially free from polysulfide compounds, one has to resort either to significant purification steps or to other methods of preparation.

More particularly, the novel carbamate ester compounds are useful as insecticides and are prepared by following one of three different methods: (a) N-(dialkylaminosulfenyl)carbamate ester with an alcohol in a suitable organic solvent in the presence of an acid such as acetic acid; (b) as above described, reacting an N-chlorosulfenylcarbamate ester with an alcohol in a suitable organic solvent in the presence of a hydrogen chloride acceptor such as pyridine or other suitable base; and (c) reacting an N-chlorosulfenylcarbamate with a metal alcoholate in a suitable organic solvent. Only in the first embodiment are the products of the reaction substantially free from polymeric sulfur compounds. In the other embodiments, unpurified carbamates are formed containing a substantial amount, about 5 to about 40 weight percent, of the corresponding polysulfide compound. In order to prepare an N-chlorosulfenylcarbamate ester, from a carbamate ester, sulfur dichloride is usually used. However, sulfur monochloride can be used instead of sulfur dichloride, resulting in a final product which contains larger amounts of polysulfide derivatives. Although not readily susceptible to easy explanation, it appears that the polysulfide compound has certain advantages over the purified compound in that it has been found to be substantially as effective as an insecticide as the purified compound on a weight basis against insects, but to have decreased toxicity on a weight basis against mammals. While it is not desired to be limited to any particular theory, it can be hypothesized that the polysulfide component of the compound serves to facilitate the incorporation, or metabolism, of the compound in insects while not having that effect in mammals; therefore, in mammals the polysulfide component of the compound serves simply as a diluent. The result is an insecticide which is not only inexpensive because of the lack of need for extraordinary purification steps but also because of the fact that the costly components of the molecules, e.g., the furan components, are present in a relatively smaller percentage of the final formulation than is the case with the pure compound. In either case, the compounds are found to have substantially reduced mammalian toxicity, e.g. as compared with other potent insecticides such as carbofuran, described in U.S. Pat. No. 3,474,171.

DETAILED DESCRIPTION

The alkoxysulfenylcarbamate esters or compounds of the invention have the formula noted below:

wherein n is 1 or a value between 1 and about 4; R is a hydrocarbyl group containing from 1 to 12 carbon atoms; $R_1$ is a hydrocarbyl group containing from 1 to 20 carbon atoms or is a 5 to 6 membered heterocyclic ring containing O or S atoms; and $R_2$ is a hydrocarbyl group containing only atoms of carbon and hydrogen, and from 1 to 24 carbon atoms, or is a substituted hydrocarbyl group of 1 to 24 carbon atoms containing, in addition to atoms of carbon and hydrogen, at least one other atom such as oxygen, sulfur, nitrogen and halogen.

More particularly, R is a hydrocarbyl (hydrocarbon) group containing only hydrogen and carbon, either aliphatic or aromatic; preferably a straight chain, branched or carbocyclic (5 or 6 membered ring) alkyl, phenylalkyl or phenyl, and is further exemplified hereinafter.

$R_1$ can be a hydrocarbyl group containing only hydrogen and carbon, either aliphatic or aromatic, including substituted or unsubstituted alkyl, cycloalkyl, phenylalkyl and naphthylalkyl; and substituted or unsubstituted aryl, such as phenyl and naphthyl; and wherein the aforementioned groups can be substituted with one or more halogen, cyano, nitro, alkyl, alkylthio and alkyoxy groups; or $R_1$ is a 5 or 6 membered heterocyclic ring containing O or S atoms, e.g., benzothienyl, furanyl, benzofuranyl and 1,3-benzodioxolyl.

Where $R_1$ is aryl, preferred examples of such aryl groups are as follows:

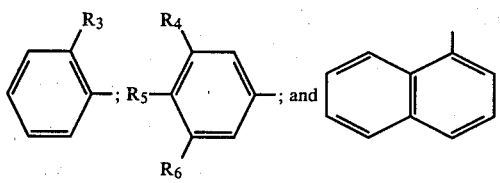

where
- $R_3$ is hydrogen, alkoxy, alkylthio, alkyl, alkylthioalkyl, 2-dioxalanyl or halogen, e.g., Cl or Br;
- $R_4$ is alkyl, alkoxy, alkoxyalkyl or halogen;
- $R_5$ is hydrogen, alkyl, halogen, alkylthio, alkoxy, dialkylamino or formyl(alkyl)amino;
- $R_6$ is hydrogen or alkyl;

and wherein the number of aliphatic carbon atoms in $R_3$, $R_4$, $R_5$ and $R_6$, individually should not exceed eight.

$R_2$ can be hydrocarbyl group, such as alkyl, cycloalkyl, bicycloalkyl, alkenyl, cycloalkenyl, bicycloalkenyl or aralkyl, all of which may be either unsubstituted or substituted with one or more chloro, bromo, fluoro, cyano, alkyl, alkoxy, alkoxycarbonyl, alkylthio or haloalkyl substituents; or $R_2$ can be a substituted hydrocarbyl group, such as aryloxyalkyl, alkoxyalkyl, arylthioalkyl, alkylthioalkyl, dialkylaminoalkyl all of which may be either unsubstituted or substituted with one or more chloro, bromo, fluoro, cyano, alkyl, alkoxy, alkoxycarbonyl, alkylthio or haloalkyl substituents.

In one group of preferred carbamate ester compounds of the invention, $R_1$ is a hydrocarbyl group containing from 1 to 12 carbon atoms, either aliphatic or aromatic, including alkyl, e.g., methyl, ethyl, isopropyl, propyl, isobutyl, cycloalkyl, e.g., cyclohexyl, phenylalkyl, naphthylalkyl, aryl, e.g., phenyl, naphthyl, alkylphenyl, e.g., tolyl, xylyl, alkylnaphthyl, any of which can contain substituents such as halogen, e.g., chlorine or bromine, alkoxy, alkylthio and dialkylamino, and R is alkyl, phenyl, phenylalkyl and naphthylalkyl groups, as exemplified above, containing 1–12 carbon atoms. Particularly preferred are those compounds where $R_1$ is alkyl, phenyl, alkylphenyl and naphthyl groups, and which can be unsubstituted or substituted, e.g., with halogen, alkoxy, dialkylamino, alkylthio groups, and the like, and especially wherein R is 3-alkylphenyl such as 3-isopropyl- and 3-sec-butylphenyl, 2-alkoxyphenyl such as 2-isopropoxyphenyl or 1-naphthyl. Particularly preferred also is the group of carbamate esters wherein $R_1$ is a heterocyclic ring, and including fused-on heterocyclic rings, containing one or two O or S atoms, and 5 to 6 members in the heterocyclic nucleus, e.g., benzofuranyl or 1,3-benzodioxolyl, and especially a 2,3-dihydro-7-benzofuranyl group having the formula (2) below, and the 1,3-benzodioxol-4-yl group having the formula (3) below:

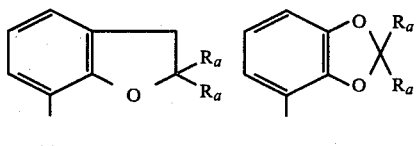

wherein $R_a$ is an alkyl group of 1 to about 4 carbon atoms, e.g., methyl, ethyl, propyl, n-butyl, and both $R_a$'s can be the same or different, and most preferably wherein $R_1$ is the 2,3-dihydro-2,2-dimethyl-7-benzofuranyl group or the 2,2-dimethyl-1,3-benzodioxol-4-yl group; and R is alkyl.

$R_2$ is all the above preferred compounds is a hydrocarbyl group containing from 1 to 24 carbon atoms, preferably alkyl, cycloalkyl or bicycloalkyl. Among the preferred alkyl groups are methyl, ethyl, n-propyl, isopropyl, n-butyl, tert-butyl, amyl, cyclopentyl, cyclohexyl, heptyl, 3-ethylamyl, 2-methylhexyl, n-hexyl, n-octyl, 4-methylheptyl, n-decyl with an increasing number of carbon atoms up to tetracosyl, or 1-adamantyl, bicyclo[4.4.0]decan-1-yl or bornyl. Particularly preferred also are those compounds where $R_2$ is alkenyl from 1 to 12 carbon atoms, e.g., allyl, geranyl, neryl, linalyl or cinnamyl. Particularly preferred also is the group of carbamate esters wherein $R_2$ is aralkyl such as phenethyl, α-naphthylmethyl, substituted or unsubstituted benzyl of the general formula (4) below:

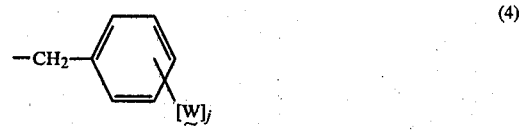

wherein W represents an alkyl group of 1 to 4 carbon atoms, an alkoxy group of 1 to 4 carbon atoms, an alkylthio group of 1 to 4 carbon atoms, halogen, j represents an integer from 1 to 5, and all W's need not necessarily be the same. Also particularly preferred are those compounds where $R_2$ is an aryloxyalkyl or arylthioalkyl of the general formula (5) below:

$$—(CH_2)_l—X—R_7 \quad (5)$$

wherein X is an oxygen or sulfur atom, l is an integer from 2 to 4, and $R_7$ represents a phenyl, α-naphthyl, a substituted phenyl of the general formula (6) below:

wherein Y represents an alkyl group of 1 to 4 carbon atoms, an alkoxy group of 1 to 4 carbon atoms, an alkythio group of 1 to 4 carbon atoms, halogen, j represents an integer from 1 to 5, and all Y's need not necessarily be the same.

Another particularly preferred class of carbamates of the invention are those wherein $R_2$ is an alkoxyalkyl or alkylthioalkyl of the general formula (7) below:

(7) wherein $R_8$ represents an alkyl group of 1 to 4 carbon atoms such as methyl, ethyl, propyl, isopropyl, n-butyl, tert-butyl or sec-butyl, X and Z are oxygen or sulfur atoms in any combination, l and m are integers from 2 to 4, and n is an integer from 0 to 2.

The N-alkoxysulfenylcarbamate esters of the invention can be prepared in accordance with a variety of methods. One preferred method for preparing the compounds substantially free of polysulfide compounds is illustrated by the general reaction set forth below:

METHOD A

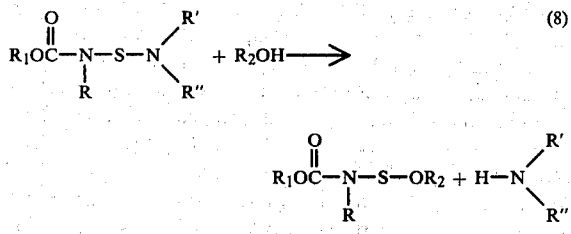

where R, $R_1$ and $R_2$ are as defined above. R' and R" may be the same or different, and each is alkyl of 1 to 8 carbon atoms which may contain an —O—, —S—, or —NR'''—linkage, [where R''' is lower (1 to 4 carbons) alkyl, benzyl, or phenyl], cycloalkyl or 3 to 6 carbon atoms, or benzyl, or R' and R" taken together with the nitrogen form a heterocyclic ring of 5 to 8 members which may contain an —O—, —S—, or —NR'''—, which heterocyclic ring may be substituted by one or more alkyl, aralkyl, aryl, or alkoxy groups. The method is exemplified by the reaction of 2,3-dihydro-2,2-dimethyl-7-benzofuranyl [(dibutylamino)thio]methylcarbamate (which can also be called dibutylamino-sulfenylcarbofuran) and is sold as "Marshal" insecticide by FMC Corporation.

The N-(dialkylaminosulfenyl)carbamate ester can react with alcohol in the presence of at least an equivalent amount of acid such as acetic acid. Such reaction is generally carried out by employing an excess of alcohol of up to 1000-fold above the stoichiometric equivalent proportion, in an inactive solvent such as dichloromethane or without using any solvents. The reaction is conveniently carried out at about room temperature, e.g., 20°–25° C., but may be carried out at about 0° to 80° C. As indicated, this method yields products with only trace amounts of polysulfide compound.

An alternative method of preparing compounds of this invention is illustrated by the general reaction scheme set forth below:

METHOD B

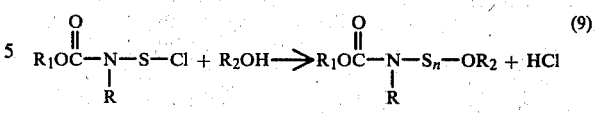

where R, $R_1$, and $R_2$ and n are as defined above. The N-chlorosulfenylcarbamate ester intermediate is formed by the reaction of the corresponding carbamate with sulfur dichloride or sulfur monochloride, preferably using pyridine as hydrogen chloride acceptor in a suitable organic solvent such as dichloromethane, tetrahydrofuran, acetonitrile, benzene, hexane and diethyl ether. Without isolation, the N-chlorosulfenylcarbamate ester intermediates can react in situ with alcohols to form N-alkoxysulfenylcarbamate esters containing polysulfide compound.

An acid acceptor or hydrogen chloride acceptor is added to aid the reaction. A preferred acid acceptor is pyridine, but other tertiary organic amines can be employed as acid acceptors, including dimethylaniline or diethylaniline, as well as numerous other acid acceptors well known to those skilled in the art. The reaction employing an organic solvent and acid acceptor can be carried out from $-20°$ C. up to an elevated temperature of about 80° C., preferably from 0° to 30° C.

When employing an organic solvent and acid acceptor, a stoichiometric molar amount of alcohol and N-chlorosulfenylcarbamate are employed. If desired, however, an excess of alcohol, e.g., up to about 100-fold molar excess based on the N-chlorosulfenylcarbamate, can be employed. If desired, deficiency of alcohol, e.g., up to about 20% molar deficiency based on the N-chlorosulfenylcarbamate, can be employed. Approximately equimolar amounts of acid acceptor and carbamate starting material generally are employed. However, excess of acid acceptor, e.g., up to about 100-fold molar excess, may be employed if desired.

It will be understood that if desired, the N-chlorosulfenylcarbamate ester starting material in reaction (9) above can be initially prepared and isolated as an intermediate compound, and such compound then reacted with the appropriate $R_2OH$ compound in a suitable organic solvent as noted in the above reaction scheme.

Another alternative method of preparing compounds of this invention is illustrated by the general reaction scheme set forth below:

METHOD C

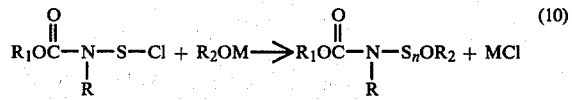

where R, $R_1$, $R_2$ and n are as defined above and M is metal, such as sodium, potassium, lithium, and tin. The N-chlorosulfenylcarbamate ester intermediate is formed by the same procedure mentioned above. Without isolation, the N-chlorosulfenylcarbamate ester intermediate dissolved in a suitable organic solvent such as diethyl ether, dichloromethane, benzene, and acetonitrile, is added into a suspension of alcoholate in a suitable organic solvent.

The reaction can be carried out from $-20°$ C. up to an elevated temperature of about 80° C., preferably from 0° to 30° C. In this reaction a stoichiometric molar amount of alcoholate and N-chlorosulfenylcarbamate are employed. If desired, however, excess of alcoholate, e.g., up to about 100-fold molar excess based on the N-chlorosulfenylcarbamate, can be employed. If desired, deficiency of alcoholate, e.g., up to about 20% molar deficiency based on the N-chlorosulfenylcarbamate, can be employed.

It will be understood that if desired, the N-chlorosulfenylcarbamate ester starting material in reaction (10) above can be initially prepared and isolated as an intermediate compound, and such compound then reacted with the appropriate $R_2OM$ compound in a suitable organic solvent as noted in the above reaction scheme.

In both methods B and C, substantial amounts of polysulfide compounds are formed, about 5 to about 40 weight percent. The pure N-alkoxysulfenylcarbamate can be obtained by subjecting the mixture of the product and its polysulfide derivatives to preparative thin-layer chromotography using a silica gel reversed-phase $KC_{18}$ plate developed with acetonitrile-water (9:1).

Examples 1 and 2 illustrate preparation of N-alkoxyfulenylcarbamate esters according to Method A in the invention.

EXAMPLE 1

Synthesis of 2,3-dihydro-2,2-dimethyl-7-benzofuranyl(methoxysulfenyl)(methyl)carbamate 2,3-Dihydro-2,2-dimethyl-7-benzofuranyl(di-n-butylaminosulfenyl)(methyl)carbamate (500 mg, 1.35 mmol) was dissolved in 18 ml methanol (14.2 g, 444 mmol) in a presence of 2.0 ml (2.10 g, 35 mmol) acetic acid and was allowed to stand for 24 hours at room temperature. The reaction mixture was evaporated to remove methanol and then added with dichloromethane (25 ml). The mixture was washed with water three (25 ml each) times. The dichloromethane solution was dried over anhydrous sodium sulfate, filtered and concentrated under vacuum. The brown liquid was purified by silica gel preparative thin-layer chromatography using hexanes-ether (7:3) as a developing solvent to give 161 mg (42%) of pure material, $n_D^{23}$ 1.5342 (light yellow oil). NMR in chloroform-d-TMS showed the following absorptions: δ 1.48 (6H, s, C(C$\underline{H}_3$)$_2$), 3.02 (2H, s, C$\underline{H}_2$), 3.57 (3H, s, N-C$\underline{H}_3$), 3.91 (3H, s, OC$\underline{H}_3$), 6.7–7.1 (3H, m, aromatic). Electron impact mass spectrum (70 eV) showed the following major peaks: m/z 284 (2.2%), 283 (M+, 9.8%), 226 (5.7%), 208 (1.5%), 195 (2.6%), 167 (5.9%), 164 (13.2%), 163 (100%), 145 (7.5%), 135 (39.2%), 120 (14.2%), 117 (10.3%), 107 (26.3%), 91 (21.6%), 77 (13.2%), 63 (33.1%).

EXAMPLE 2

Synthesis of 2,3-dihydro-2,2-dimethyl-7-benzofuranyl(ethoxysulfenyl)(methyl)carbamate 2,3-Dihydro-2,2-dimethyl-7-benzofuranyl(di-n-butylaminosulfenyl)(methyl)carbamate (740 mg, 2.0 mmol) was dissolved in 27 ml ethanol (21.3 g, 463 mmol) in a presence of 3.0 ml (3.15 g, 52.5 mmol) acetic acid and was allowed to stand for 96 hours at room temperature. The mixture was worked up similar to Example 1 and a sample of the oily product was purified by silica gel thin-layer chromatography using hexanes-ether (7:3) as a developing solvent to give 234 mg (39%) of pure material, $n_D^{23}$ 1.5250 (light yellow oil). NMR (CDCl$_3$—TMS): δ 1.28 (3H, t, OCH$_2$C$\underline{H}_3$), 1.43 (6H, s, C(C$\underline{H}_3$)$_2$), 3.02 (2H, s, benzyl), 3.55 (3H, s, N-C$\underline{H}_3$), 4.20 (2H, q, OC$\underline{H}_2$CH$_3$), 6.7–7.1 (3H, m, aromatic); mass spectrum (70 eV) m/z (relative intensity) 298 (4.8), 297 (M+, 19.7), 269 (1.1), 252 (1.4), 240 (8.0), 195 (5.6), 164 (51.3), 163 (100), 149 (14.3), 135 (43.6), 134 (10.8), 107 (33.8), 105 (15.4), 91 (34.2).

Examples 3 through 11 illustrate preparation of N-alkoxysulfenylcarbamate esters according to Method B in the invention.

EXAMPLE 3

Synthesis of 2,3-dihydro-2,2-dimethyl-7-benzofuranyl(isopropoxysulfenyl)(methyl)carbamate Sulfur dichloride (5.2 g, 0.051 mol) in dichloromethane (20 ml) was added to a stirred solution of carbofuran (11.0 g, 0.050 mol) in dichloromethane (100 ml) at −5° C. The resulting mixture was maintained at 0° to 5° C. while a solution of triethylamine (6.0 g, 0.059 mol) in dichloromethane (20 ml) was added dropwise with stirring over 30 minutes. The reaction mixture was allowed to come to room temperature and stirred for 3 hours. To the resulting mixture was added dropwise a solution of 2-propanol (5.0 g, 0.050 mol) and triethylamine (6.0 g, 0.059 mol) in dichloromethane at 0° C. After stirring an additional 3 hours at 0° C., the mixture was allowed to come to room temperature and washed 3 times with water. After drying over anhydrous sodium sulfate and evaporation, the residue was dissolved in hexanes and allowed to stand until carbofuran (2.5 g) and N,N'-biscarbofuran sulfide (2.9 g) precipitated. Evaporation of the filtrate yielded a viscous oily substance (8.1 g). The crude substance (2.0 g) was purified by silica gel preparative thin-layer chromatography using hexanes-ether (7:3) as a developing solvent to give 1.4 g oily product. NMR spectrum suggested that the product is a mixture of N-isopropoxysulfenylcarbofuran (87%) and its polysulfide derivative (n≧2, 13%).

To remove the polysulfide impurities, small amounts of the mixture were subjected to preparative thin-layer chromatography using silica gel reversed-phase $KC_{18}$ plate, developed with acetonitrile-water (9:1) and pure material $n_D^{23}$ 1.5402 (light yellow oil) was obtained with a yield of 36%; NMR (CDCl$_3$—TMS): δ 1.25 (6H, d, J=6.1 Hz, OCH(C$\underline{H}_3$)$_2$), 1.42 (6H, s, C(C$\underline{H}_3$)$_2$), 3.02 (2H, br.s, C$\underline{H}_2$), 3.53 (3H, s, N—C$\underline{H}_3$), 4.40 (1H, sep, OC$\underline{H}$(CH$_3$)$_2$), 6.7–7.1 (3H, m, aromatic); mass spectrum (70 eV) m/z (relative intensity) 311 (4.1), 269 (16.3), 195 (8.0), 191 (2.3), 164 (100).

EXAMPLE 4

Synthesis of 2,3-dihydro-2,2-dimethyl-7-benzofuranyl(hexyloxysulfenyl)(methyl)carbamate To a solution of 2,3-dihydro-2,2-dimethyl-7-benzofuranyl(chlorosulfenyl)(methyl)carbamate (0.050 mol) prepared from 11.0 g of 2,3-dihydro-2,2-dimethyl-7-benzofuranyl methylcarbamate and 5.2 g of sulfur dichloride in dichloromethane as described in Example 3, was added dropwise with a solution of 1-hexanol (5.1 g, 0.050 mol) and triethylamine (6.0 g, 0.059 mol) in dichloromethane at 0° C. The mixture was stirred for 3 hours at 0° C. and worked up similarly to previous examples to obtain the target compound containing 20 percent by weight of the polysulfide derivative.

A sample was purified by thin-layer chromatography as previously described to give pure material, $n_D^{23}$ 1.5164. Yield: 38%; NMR (CDCl$_3$—TMS): δ 0.90 (3H, br.t, O(CH$_2$)$_5$CH$_3$), 1.0–1.8 (8H, m, OCH$_2$(CH$_2$)$_4$CH$_3$), 1.48 (6H, s, C(CH$_3$)$_2$), 3.03 (2H, s, benzyl), 3.57 (3H, s, N-CH$_3$), 4.10 (2H, br.t, OCH$_2$(CH$_2$)$_4$), 6.7–7.1 (3H, m, aromatic); mass spectrum (70 eV) m/z (relative intensity) 353 (M+ 5.6) 269 (11.3), 195 (6.9), 191 (3.1), 164 (100).

EXAMPLE 5

Synthesis of 2,3-dihydro-2,2-dimethyl-7-benzofuranyl(cyclohexyloxysulfenyl)(methyl)carbamate To a solution of 2,3-dihydro-2,2-dimethyl-7-benzofuranyl(chlorosulfenyl)(methyl)-carbamate (0.040 mol) prepared from 8.9 g of 2,3-dihydro-2,2-dimethyl-7-benzofuranyl methylcarbamate and 4.1 g of sulfur dichloride in dichloromethane as described in Example 3, was added dropwise with a solution of cyclohexanol (4.1 g, 0.040 mol) and triethylamine (4.8 g, 0.047 mol) in dichloromethane at 0° C. The mixture was stirred for 3 hours at 0° C. and worked up similarly to previous examples to obtain the target compound containing 5 percent by weight of the polysulfide derivative.

A sample was purified by thin-layer chromatography as previously described to give pure material, $n_D^{23}$ 1.5190. Yield: 49%; NMR (CDCl$_3$—TMS): δ 1.0–2.2 (10H, br.m., OCH(CH$_2$)$_5$), 1.46 (6H, s, C(CH$_3$)$_2$), 3.03 (2H, br.s, benzyl), 3.55 (3H, s, N-CH$_3$), 4.05 (1H, br. peak, OCH—(CH$_2$)$_5$), 6.7–7.2 (3H, m, aromatic); mass spectrum (70 eV) m/z 351 (M+).

EXAMPLE 6

Synthesis of 2,3-dihydro-2,2-dimethyl-7-benzofuranyl(benzyloxysulfenyl)(methyl)carbamate To a solution of 2,3-dihydro-2,2-dimethyl-7-benzofuranyl(chlorosulfenyl)(methyl)carbamate (0.050 mol) prepared from 11.0 g of 2,3-dihydro-2,2-dimethyl-7-benzofuranyl methylcarbamate and 5.2 g of sulfur dichloride in dichloromethane as described in Example 3, was added dropwise with a solution of benzyl alcohol (5.4 g, 0.050 mol) and triethylamine (6.0 g, 0.059 mol) in dichloromethane at 0° C. The mixture was stirred for 3 hours at 0° C. and worked up similarly to previous examples to obtain the target compound containing 20 percent by weight of the polysulfide derivative.

A sample was purified by thin-layer chromatography as previously described to give pure material, m.p. 42°–45° C. Yield: 41%; NMR (CDCl$_3$—TMS): δ 1.40 (6H, s, C(CH$_3$)$_2$), 3.00 (2H, s, benzyl of carbofuran moiety), 3.53 (3H, s, N—CH$_3$), 5.13 (2H, s, OCH$_2$—C$_6$H$_5$), 6.7–7.1 (3H, m, aromatic of carbofuran moiety), 7.3–7.5 (5H, m, aromatic of benzyl group); mass spectrum (70 eV) m/z (relative intensity) 359 (M+, 2.3), 285 (0.8), 254 (12.9), 195 (1.4), 191 (0.6), 163 (14.2), 108 (5.8), 107 (5.5), 91 (100).

EXAMPLE 7

Synthesis of 2,3-dihydro-2,2-dimethyl-7-benzofuranyl(dodecyloxysulfenyl)(methyl)carbamate To a solution of 2,3-dihydro-2,2-dimethyl-7-benzofuranyl(chlorosulfenyl)(methyl)carbamate (0.040 mol) prepared from 8.9 g of 2,3-dihydro-2,2-dimethyl-7-benzofuranyl methylcarbamate and 4.1 g of sulfur dichloride in dichloromethane as described in Example 3, was added dropwise with a solution of 1-dodecanol (7.6 g, 0.040 mol) and triethylamine (4.8 g, 0.047 mol) in dichloromethane at 0° C. The mixture was stirred for 2 hours at 0° C. and then 1 hour at 23° C., and worked up similarly to previous examples to obtain the target compound containing 19 percent by weight of the polysulfide derivative.

A sample was purified by thin-layer chromatography as previously described to give pure material, $n_D^{23}$ 1.5030. Yield: 43%; NMR (CDCl$_3$—TMS): δ 0.89 (3H, br.t, O(CH$_2$)$_{11}$CH$_2$), 1.1–1.9 (20H, br. m, OCH$_2$—(CH$_2$)$_{10}$CH$_3$), 2.98 (2H, br.s, benzyl), 3.57 (3H, s, N—CH$_3$), 4.11 (2H, br.t, OCH$_2$(CH$_2$)$_{10}$CH$_3$), 6.7–7.2 (3H, m, aromatic); mass spectrum (70 eV) m/z 437 (M+).

EXAMPLE 8

Synthesis of 2-isopropoxyphenyl(butoxysulfenyl)(methyl)

To a solution of 2-isopropoxyphenyl(chlorosulfenyl)-(methyl)carbamate (0.0091 mol) prepared from 1.9 g of 2-isopropoxyphenyl(chlorosulfenyl)(methyl)carbamate (0.0091 mol) prepared from 1.9 g of 2-isopropoxyphenyl methylcarbamate and 1.0 g of sulfur dichloride in dichloromethane, was added dropwise with a solution of 1-butanol (1.0 g, 0.014 mol) and triethylamine (1.2 g, 0.0097 mol) in dichloromethane at 0° C. The mixture was stirred for 3 hours at 0° C. and worked up similarly to previous examples to obtain the target compound containing 15 percent by weight of the polysulfide derivative.

A sample was purified by thin-layer chromatography as previously described to give pure material. $n_D^{23}$ 1.5103. Yield: 38%; NMR (CDCl$_3$—TMS); δ 0.91 (3H, t, O(CH$_2$)$_3$CH$_3$), 0.30 (6H, d, OCH(CH$_3$)$_2$), 1.1–1.8 (4H, m, OCH$_2$(CH$_2$)$_2$CH$_3$), 3.59 (3H, s, N—CH$_3$), 4.11 (2H, t, OCH$_2$(CH$_2$)$_2$CH$_3$), 4.54 (1H, sep, OCH(CH$_3$)$_2$), 6.8–7.4 (4H, m, aromatic); mass spectrum (70 eV) m/z 313 (M+).

EXAMPLE 9

Synthesis of 2-isopropoxyphenyl(benzyloxysulfenyl)(methyl)carbamate

To a solution of 2-isopropoxyphenyl(chlorosulfenyl)-(methyl)carbamate (0.0091 mol) prepared from 1.9 g of 2-isopropoxyphenyl methylcarbamate and 1.0 g of sulfur dichloride in dichloromethane, was added dropwise with a solution of benzyl alcohol (1.1 g, 0.010 mol) and triethylamine (1.2 g, 0.090 mol) in dichloromethane at 0° C. The mixture was stirred for 3 hours at 0° C. and worked up similarly to previous examples to obtain the target compound containing 16 percent by weight of the polysulfide derivative.

A sample was purified by thin-layer chromatography as previously described to give pure material, $n_D^{23}$ 1.5552. Yield: 42%; NMR (CDCl$_3$—TMS): δ 1.26 (6H, d, OCH(CH$_3$)$_2$), 3.56 (3H, s, N—CH$_3$), 4.51 (1H, sep, OCH(CH$_3$)$_2$), 5.10 (2H, s, OCH$_2$—C$_6$H$_5$), 6.8–7.5 (9H, m, aromatic); mass spectrum (70 eV) m/z 347 (M+).

EXAMPLE 10

Synthesis of 3-isopropylphenyl(butoxysulfenyl)(methyl)carbamate

To a solution of 3-isopropylphenyl(chlorosulfenyl)-(methyl)carbamate (0.010 mol) prepared from 1.9 g of 3-isopropylphenyl methylcarbamate and 1.0 g of sulfur dichloride in dichloromethane was added dropwise with a solution of 1-butanol (1.0 g, 0.014 mol) and triethylamine (1.2 g, 0.0097 mol) in dichloromethane at 0° C. The mixture was stirred for 3 hours at 0° C. and worked up similarly to previous examples to obtain the target compound containing 14 percent by weight of the polysulfide derivative.

A sample was purified by thin-layer chromatography as previously described to give pure material, $n_D^{23}$ 1.5128. Yield: 15%; NMR (CDCl$_3$—TMS): δ 0.91 (3H, t, O(CH$_2$)$_3$CH$_3$), 1.25 (6H, d, CH(CH$_3$)$_2$), 1.2–1.8 (4H, m, OCH$_2$(CH$_2$)$_2$CH$_3$), 2.91 (1H, sep, CH(CH$_3$)$_2$), 3.59 (3H, s, N—CH$_3$), 4.07 (2H, t, OCH$_2$(CH$_2$)$_2$CH$_3$), 6.9–7.5 (4H, m, aromatic); mass spectrum (70 eV) m/z 297 (M+).

EXAMPLE 11

Synthesis of 3-isopropylphenyl(benzyloxysulfenyl)(methyl)carbamate

To a solution of 3-isopropylphenyl(chlorosulfenyl)-(methyl)carbamate (0.010 mol) prepared from 1.9 g of 3-isopropylphenyl methylcarbamate and 1.0 g of sulfur dichloride in dichloromethane, was added dropwise with a solution of benzyl alcohol (1.0 g, 0.0092 mol) and triethylamine (1.2 g, 0.0097 mol) in dichloromethane at 0° C. The mixture was stirred for 3 hours at 0° C. and worked up similarly to previous examples to obtain the target compound containing 23 percent by weight of the polysulfide derivative.

A sample was purified by thin-layer chromatography as previously described to give pure material, $n_D^{23}$ 1.5574. Yield: 26%; NMR (CDCl$_3$—TMS): δ 1.24 (6H, d, CH(CH$_3$)$_2$), 2.90 (1H, sep, CH(CH$_3$)$_2$), 3.54 (3H, s, N-CH$_3$), 5.09 (2H, s, OCH$_2$—C$_6$H$_5$), 6.8–7.5 (9H, m, aromatic); mass spectrum (70 eV) m/z 331 (M+).

The following compounds further illustrate the N-alkoxysulfenylcarbamates prepared according to Method B in this invention:

| Example No. | Compound Name |
| --- | --- |
| 12 | 2,3-Dihydro-2,2-dimethyl-7-benzofuranyl (1-ethyl-propoxysulfeny)(methyl)carbamate containing 5 percent by weight of the polysulfide derivative. |
| 13 | 2,3-Dihydro-2,2-dimethyl-7-benzofuranyl (tert-butoxysulfenyl)(methyl)carbamate containing 6 percent by weight of the polysulfide derivative. |
| 14 | 2,3-Dihydro-2,2-dimethyl-7-benzofuranyl (methyl)-(octyloxysulfenyl)carbamate containing 15 percent by weight of the polysulfide derivative. |
| 15 | 2,3-Dihydro-2,2-dimethyl-7-benzofuranyl (decyloxysulfenyl)(methyl)carbamate containing 18 percent by weight of the polysulfide derivative. |
| 16 | 2,3-Dihydro-2,2-dimethyl-7-benzofuranyl (P—methoxybenzyloxysulfenyl)(methyl)carbamate containing 20 percent by weight of the polysulfide derivative. |
| 17 | 2,3-Dihydro-2,2-dimethyl-7-benzofuranyl (P—tert-butylbenzyloxysulfenyl)(methyl)carbamate containing 15 percent by weight of the polysulfide derivative. |
| 18 | 2,3-Dihydro-2,2-dimethyl-7-benzofuranyl (methyl)(octadecyloxysulfenyl)carbamate containing 15 percent by weight of the polysulfide derivative. |

Example 19 illustrates preparation of N-alkoxysulfenylcarbamate ester according to Method C in the invention.

EXAMPLE 19

Synthesis of 2,3-dihydro-2,2-dimethyl-7-benzofuranyl(ethoxysulfenyl)(methyl)carbamate 2,3-Dihydro-2,2-dimethyl-7-benzofuranyl(chlorosulfenyl)(methyl)carbamate (0.020 mol) was prepared from 4.5 g (0.020 mol) of 2,3-dihydro-2,2-dimethylbenzofuranyl methylcarbamate and 2.0 g (0.019 mol) of sulfur dichloride in dichloromethane as described in Example 3. The reaction mixture was filtered to remove the hydrochloride and evaporated to remove dichloromethane. The residue was added with ether (20 ml) and filtered. After evaporation of the solvent, the oil obtained was added into a stirred suspension of sodium ethoxide (1.6 g, 0.024 mol) in ether (100 ml) at 0° C. and stirred for 1 hour at 0° C. The reaction mixture was worked up similarly to previous examples.

A sample was purified by thin-layer chromatography as previously described to give light yellow oil. The TLC properties and NMR and MS date of this compound agreed with those of 2,3-dihydro-2,2-dimethyl-benzofuranyl-7(ethoxysulfenyl)(methyl)carbamate prepared by Method A as described in Example 2.

Examples 20 and 21 illustrate the preparation of N-alkoxysulfenylcarbamate esters by using sulfur monochloride instead of sulfur dichloride, according to Method B in the invention, and separation of the individual components of the polysulfide derivatives of the N-alkoxysulfenylcarbamate.

EXAMPLE 20

Synthesis of 2,3-dihydro-2,2-dimethyl-7-benzofuranyl(hexyloxysulfenyl)(methyl)carbamate and polysulfide derivatives Sulfur monochloride (6.8 g, 0.050 mol) in dichloromethane (20 ml) was added to a stirred solution of carbofuran (11.0 g, 0.050 mol) in dichloromethane (80 ml) at −5° C. The resulting mixture was maintained at 0° to 5° C. while a solution of triethylamine (5.5 g, 0.054 mol) in dichloromethane (25 ml) was added dropwise with stirring over 30 minutes. The reaction mixture was allowed to come to room temperature and stirred for 3 hours. To the resulting mixture was added dropwise a solution of 1-hexanol (5.2 g, 0.051 mol) and triethylamine (5.5 g, 0.054 mol) in dichloromethane (20 ml) at 0° C. After stirring an additional 3 hours at 0° C., the mixture was allowed to come to room temperature and worked up similarly to previous examples to obtain the target compound containing 36 percent by weight of the polysulfide derivative (overall yield: 66%).

The crude substance (2.6 g) was purified by silica gel preparative thin-layer chromatography using hexanes-ether (7:3) as a developing solvent to give 1.60 g of oily product. This oil (1.57 g) was further subjected to preparative thin layer chromatography using benzene-acetonitrile (49:1) as a solvent. Fraction 1 (Rf 0.69 0.77)

and Fraction 2 (Rf 0.47–0.69) were extracted with dichloromethane. Evaporation of the solvent gave 208 mg fraction 1 and 1.05 g fraction 2.

Fraction 1 was a mixture of polysulfide derivatives ($N \geq 3$) of 2,3-dihydro-2,2-dimethyl-7-benzofuranyl(hexyloxysulfenyl)(methyl)carbamate, structure shown as below:

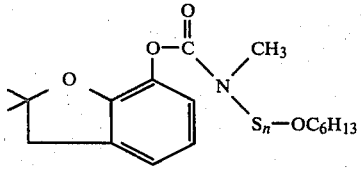

$n_D^{23}$ 1.5809. NMR (CDCl$_3$—TMS): δ 0.90 (3H, br.t, O(CH$_2$)$_5$CH$_3$), 1.0–1.8 (8H, m, OCH$_2$—(CH$_2$)$_4$CH$_3$), 1.48 (6H, s, C(CH$_3$)$_2$), 3.05 (2H, s, benzyl), 3.37–3.47 (3H, m, N—CH$_3$), 3.92 (2H, t, OCH$_2$(CH$_2$)$_4$), 6.7–7.1 (3H, m, aromatic); mass spectrum (70 eV) m/z 481, 449, 417, 385 (molecular ion peaks).

Fraction 2 (606 mg) was further subjected to preparative thin-layer chromatography using silica gel reversed-phase plate and acetonitrile (1st migration) and acetonitrile-water (9:1, 2nd migration) as solvents. Fraction 2-a (Rf 0.67–0.75) and 2-b (Rf 0.56–0.66) were extracted with ether. Evaporation of the solvent gave 282 mg 2-a and 204 mg 2-b. The TLC properties and NMR and MS data of 2-a agreed with those of 2,3-dihydro-2,2-dimethyl-7-benzofuranyl(hexyloxysulfenyl)-(methyl)carbamate (n=1 in the above structure) prepared by Method B as described in Example 4.

Fraction 2-b was the disulfide derivative of 2,3-dihydro-2,2-dimethyl-7-benzofuranyl(hexyloxysulfenyl)-(methyl)carbamate (n=2 in the above structure). $n_D^{23}$ 1.5300. NMR (CDCl$_3$—TMS): δ 0.90 (3H, br.t, O(CH$_2$)$_5$CH$_3$), 1.0–1.8 (8H, m, O—CH$_2$—(CH$_2$)$_4$CH$_3$), 1.48 (6H, s, C(CH$_3$)$_2$), 3.05 (2H, s, benzyl), 3.38 (3H, s, N—CH$_3$), 3.90 (2H, t, OCH$_2$(CH$_2$)$_4$), 6.7–7.1 (3H, m, aromatic); mass spectrum (70 eV) m/z (relative intensity) 385 (M+ 1.2) 353(0.3), 328(1.1), 269(0.6), 195(1.4), 167(4.1), 164 (19.7) 163 (100).

EXAMPLE 21

Synthesis of 2,3-dihydro-2,2-dimethyl-7-benzofuranyl(methoxysulfenyl)(methyl)carbamate and polysulfide derivatives To a solution of 2,3-dihydro-2,2-dimethyl-7-benzofuranyl(chlorosulfenyl)(methyl)carbamate (0.050 mol) prepared from 11.0 g (0.050 mol) of 2,3-dihydro-2,2-dimethyl-7-benzofuranyl methylcarbamate and 6.8 g of sulfur monochloride in dichloromethane as described in Example 20, was added dropwise a solution of methanol (1.60 g, 0.050 mol) and triethylamine (6.0 g, 0.059 mol) in dichloromethane at 0° C. The mixture was stirred for 3 hours at 0° C. and worked up similarly to previous examples to obtain the target compound containing 32% by weight of the polysulfide derivative (overall yield: 10%).

A sample was purified by silica gel thin-layer chromatography and silica gel reversed-phase thin-layer chromatography as described in Example 20 to give Fraction 1, Fraction 2-a and Fraction 2-b. Fraction 1 was a mixture of polysulfide derivative of 2,3-dihydro-2,2-dimethyl-7-benzofuranyl(methoxysulfenyl)(methyl)carbamate (n≧3 in the structure below)

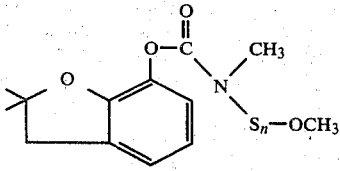

NMR (CDCl$_3$—TMS): δ 1.50 (6H, s, C(CH$_3$)$_2$), 3.05 (2H, s, CH$_2$), 3.36–3.40 (3H, m, N—CH$_3$), 3.78 (3H, s, OCH$_3$), 6.7–7.1 (3H, m, aromatic). The TLC properties and NMR and MS data of Fraction 2-a agreed with those of 2,3-dihydro-2,2-dimethyl-7-benzofuranyl(methoxysulfenyl)(methyl)carbamate (n=1 in the above structure) prepared by Method A as described in Example 1.

Fraction 2-b was the disulfide derivative of 2,3-dihydro-2,2-dimethyl-7-benzofuranyl(methoxysulfenyl)(methyl)carbamate (n=2 in the above structure) $n_D^{23}$ 1.5500. NMR (CDCl$_3$—TMS): δ 1.48 (6H, s, C(CH$_3$)$_2$, 3.05 (2H, s, CH$_2$), 3.37(3H, s, N—CH$_3$), 3.75 (3H, s, OCH$_3$), 6.7–7.1 (3H, m, aromatic); mass spectrum (70 eV) m/z 315 (M+).

The insecticidal N-alkoxysulfenylcarbamate esters of the invention may be formulated with the usual carriers including additives and extenders used in the preparation of insecticidal compositions. Thus, the toxicants of this invention like most insecticidal agents, are generally not applied full strength, but are incorporated with the adjuvants and carriers normally employed for facilitating the dispersion of active ingredients, recognizing the accepted fact that the formulation and mode of application of a toxicant may affect the activity of the material.

The present compounds may be made into liquid concentrates by solution or emulsification in suitable liquids such as organic solvents, and into solid concentrates by admixing with talc, clays, and other known solid carriers used in the insecticide art. These concentrates are compositions containing about 5–50% toxicant and the rest inert material which includes dispersing agents, emulsifying agents, and wetting agents. The concentrates are diluted for practical application, with water or other liquid for liquid sprays or with additional solid carrier for application as a dust or granular formulation.

The concentration of the toxicant in the dilution generally used for application is normally in the range of about 2% to about 0.001%. Many variations of spraying and dusting compositions in the art may be used, by substituting a compound of this invention into compositions known or apparent to the art.

Insecticidal compositions may be formulated and applied with other active ingredients, including other insecticides, nematicides, acaricides, fungicides, plant regulators, fertilizers, etc. In applying the chemicals, it is obvious that an effective amount and concentration of the carbamate ester compounds of the invention should be employed.

BIOLOGICAL ACTIVITY

Representative compounds of the N-alkoxysulfenylcarbamate esters of the invention were tested for insecticidal activity against house flies, *Musca domestica*. Stock 1% concentrated solutions of each of the test compounds were made in acetone, and such solutions diluted with acetone to a concentration of 0.001–0.1%.

House flies were treated topically on the notum by 1 μl of each of the diluted acetone solutions and percent mortality was counted 24 hours after application. Insects were held at constant temperature of 60° F.

Mammalian toxicity was determined against Swiss white mice. The test compound was applied orally using corn oil as the carrier. Results are given as $LD_{50}$ in mg of compound per kg body weight. The toxicological data for a number of typical N-alkoxysulfenylcarbamates of the invention are summarized in Table 1 below:

TABLE 1

Toxicity* of N—Alkoxysulfenylcarbamate of Examples 1 to 18 Against House Flies and White Mice

| Compound of example | Polysulfide derivative % | House flies $LD_{50}$ (μg/g) | Mice $LD_{50}$ (mg/kg) |
| --- | --- | --- | --- |
| 1 | trace | 15.5 | 43 |
| 2 | trace | 15.8 | 46 |
| 3 | 13 | 31.0 | 55–70 |
| 4 | 20 | 9.3 | 88 |
| 5 | 5 | 21.5 | 69 |
| 6 | 20 | 7.5 | 59 |
| 7 | 19 | 21.0 | 340 |
| 8 | 15 | 46.0 | >1000 |
| 9 | 16 | 30.0 | >1000 |
| 10 | 14 | 120.0 | 130 |
| 11 | 23 | 175.0 | 210 |
| 12 | 5 | 21.0 | 63 |
| 13 | 6 | 20–30 | 75 |
| 14 | 15 | 13.0 | 100 |
| 15 | 18 | 7.3 | 135 |
| 16 | 20 | 13.8 | 108 |
| 17 | 15 | 15.5 | 98 |
| 18 | 15 | 75.0 | ≧1000 |

*Samples used in toxicity evaluations contained the corresponding polysulfide derivatives in the amounts indicated The term "$LD_{50}$" represents the dose needed to kill 50% of the test animals. In interpreting the values in the table above, the lower the value for $LD_{50}$ for house flies, the greater the insecticidal potency or toxicity of that particular compound. On the other hand, the higher the value of $LD_{50}$ for mice, the lower the mammalian toxicity or the greater is the mammalian safety of such compound.

The relatively low values for the various compounds of the invention listed in Table 1 for $LD_{50}$ for house flies indicate high toxicity of the invention compounds as against the insect. Thus, for example, the parent material of the compounds of Examples 1 to 7 and 12 to 18 of Table 1, carbofuran, which is 2,3-dihydro-2,2-dimethyl-7-benzofuranyl methylcarbamate, has an $LD_{50}$ value for house flies, of about 11.0. The $LD_{50}$ values for house flies of the related invention compounds of Examples 1 through 7 and 12 through 18 are comparable, ranging from 7.3 to 31 except for Example 18 ($LD_{50}$=75 μg/g), thus showing comparable insecticidal toxicity of such invention compounds to the potent insecticide carbofuran. However, and of particular significance, the mammalian toxicity of the invention compounds of Examples 1 to 7 and 12 to 18 above, as indicated by their high $LD_{50}$ values ranging from 43 to 1000 for mice, is low, as compared to the much higher toxicity as indicated by an $LD_{50}$ value of 11, found for the parent carbamate ester insecticide, carbofuran. Also, compound 9 is of comparable toxicity to house flies as the parent carbamate propoxur, which is 2-isopropoxyphenyl methylcarbamate. However, compound 9 is much safer to mammals ($LD_{50}$>1000 mg/kg) as compared to propoxur (62 mg/kg).

Toxicological data for several of the polysulfide derivatives of two N-alkoxysulfenylcarbamates of the invention are summarized in Table 2 below:

TABLE 2

Toxicity of Several Polysulfide Derivatives of N—Alkoxysulfenylcarbamate Against House Flies and White Mice

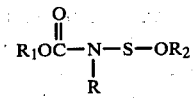

| R | n | House flies $LD_{50}$ (μg/g) | Toxicity Mice $LD_{50}$ (mg/kg) |
| --- | --- | --- | --- |
| $CH_2(CH_2)_4CH_3$ | 1 to n (polysulfide mixture) | 14.5 | 62 |
| $CH_2(CH_2)_4CH_3$ | 1 | 9.3 | 37 |
| $CH_2(CH_2)_4CH_3$ | 2 | 13.0 | 72 |
| $CH_2(CH_2)_4CH_3$ | ≧3 | 22.0 | 105 |
| $CH_3$ | 1 to n (polysulfide mixture) | 18.8 | 40 |
| $CH_3$ | 1 | 15.5 | 43 |
| $CH_3$ | 2 | 20.5 | 48 |
| Carbofuran | | 11.0 | 11–19 |

Compared to 2,3-dihydro-2,2-dimethyl-7-benzofuranyl (hexyloxysulfenyl)(methyl)carbamate or 2,3-dihydro-2,2-dimethyl-7-benzofuranyl (methoxysulfenyl)(methyl)carbamate, the polysulfide derivatives showed comparable insecticidal toxicity against houseflies, $LD_{50}$ values ranging from 13.0 to 22.0, and some mammalian toxicity ($LD_{50}$ 50-105 mg/kg) against mice. Therefore, the polysulfide derivatives are comparable in insecticidal activity to the potent insecticide carbofuran but much safer to mammals than carbofuran.

Thus, the above tables show that the N-alkoxysulfenylcarbamate esters of the invention have high insecticidal activity or potency, but have substantially reduced mammalian toxicity or substantially greater mammalian safety.

While we have described particular embodiments of the invention for purposes of illustration, it will be understood that various changes and modifications within the spirit of the invention can be made, and the invention is not to be taken as limited except by the scope of the appended claims.

What is claimed is:

1. A composition having pesticidal activity comprising about 60 to 95 percent by weight of a carbamate of the formula:

$$R_1OC(=O)-N(R)-S-OR_2$$

wherein R is a hydrocarbyl group containing from 1 to 12 carbon atoms; $R_1$ is a hydrocarbyl group containing from 1 to 20 carbon atoms or is a benzoheterocyclic ring containing 5 or 6 members in the heterocyclic portion, said heterocyclic portion containing one or two O or S atoms; and $R_2$ is a hydrocarbyl group containing only atoms of carbon and hydrogen and from 1 to 24 carbon atoms, or is a substituted hydrocarbyl group of 1-24 carbon atoms containing, in addition to atoms of carbon and hydrogen, at least one other atom; and from about 5 to about 40 percent by weight of a polysulfide derivative of said carbamate of the formula:

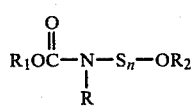

wherein n is an integer between 2 and about 4 and the other variables are as above.

2. A composition as defined in claim 1 wherein $R_2$ is selected from the group consisting of methyl, ethyl, isopropyl, hexyl, cyclohexyl, benzyl, dodecyl, n-butyl, 1-ethylpropyl, tert-butyl, octyl, decyl, P-methoxybenzyl and octadecyl.

3. A composition as defined in claim 1 which is selected from the group consisting of 2,3-dihydro-2,2-dimethyl-7-benzofuranyl(methoxysulfenyl)(methyl)carbamate; 2,3-dihydro-2,2-dimethyl-7-benzofuranyl(ethoxysulfenyl)-(methyl)carbamate; 2,3-dihydro-2,2-dimethyl-7-benzofuranyl(isopropoxysulfenyl)(methyl)-carbamate; 2,3-dihydro-2,2-dimethyl-7-benzofuranyl(hexyloxysulfenyl)(methyl)carbamate; 2,3-dihydro-2,2-dimethyl-7-benzofuranyl(cyclohexyloxysulfenyl)(methyl)carbamate; 2,3-dihydro-2,2-dimethyl-7-benzofuranyl(benzyloxysulfenyl)(methyl)carbamate; 2,3-dihydro-2,2-dimethyl-7-benzofuranyl(dodecyloxysulfenyl)(methyl)carbamate; 2-isopropoxyphenyl(butoxysulfenyl)(methyl)carbamate; 2-isopropoxyphenyl(benzyloxysulfenyl)(methyl)carbamate; 3-isopropylphenyl(butoxysulfenyl)(methyl)carbamate; 3-isopropylphenyl(benzyloxysulfenyl)(methyl)carbamae; 2,3-dihydro-2,2-dimethyl-7-benzofuranyl(1-ethylpropoxysulfenyl)(methyl)carbamate; 2,3-dihydro-2,2-dimethyl-7-benzofuranyl(tert-butoxysulfenyl)(methyl)carbamate; 2,3-dihydro-2,2-dimethyl-7-benzofuranyl(methyl)(octyloxysulfenyl)carbamate; 2,3-dihydro-2,2-dimethyl-7-benzofuranyl (decyloxysulfenyl)(methyl)carbamate; 2,3-dihydro-2,2-dimethyl-7-benzofuranyl(P-methoxybenzyloxysulfenyl)(methyl)carbamate; 2,3-dihydro-2,2-dimethyl-7-benzofuranyl(P-tert-butyl-benzyloxysulfenyl)(methyl)carbamate; 2,3-dihydro 2,2-dimethyl-7-benzofuranyl(methyl)(octadecyloxysulfenyl)carbamate.

4. An insecticidal composition comprising an insecticidally effective amount of a composition as defined in claim 1 in combination with a suitable carrier.

5. An insecticidal composition comprising an insecticidally effective amount of a composition as defined in claim 2 in combination with a suitable carrier.

6. An insecticidal composition comprising an insecticidally effective amount of a composition as defined in claim 3 in combination with a suitable carrier.

7. The method of controlling insects which comprises applying to the sites of infestation an insecticidally effective amount of a composition as defined in claim 1.

8. The method of controlling insects which comprises applying to the sites of infestation an insecticidally effective amount of a composition as defined in claim 2.

9. The method of controlling insects which comprises applying to the sites of infestation an insecticidally effective amount of a composition as defined in claim 3.

* * * * *

UNITED STATES PATENT AND TRADEMARK OFFICE
CERTIFICATE OF CORRECTION

PATENT NO. : 4,394,383

DATED : July 19, 1983

INVENTOR(S) : M. Kawata et al

It is certified that error appears in the above-identified patent and that said Letters Patent are hereby corrected as shown below:

Col. 4, line 4, delete first occurrence of "is" and substitute "in".

Col. 9, line 31, delete "OC$\underline{H}$-(CH$_2$)$_5$" and substitute "OC$\underline{H}$(CH$_2$)$_5$"

Col. 9, line 32, delete "V" and substitute "$\bar{V}$".

Co. 9, line 57, delete "V" and substitute "$\bar{V}$".

Col. 10, line 22, after "(methyl)" add "carbamate".

Col. 10, line 65, delete "N-CH$_3$)" and substitute "N-C$\underline{H}_3$)"

Col. 10, line 66, delete "OCH(CH$_3$)" and substitute "OC$\underline{H}$(CH$_3$)"

Col. 10, line 66, delete "OC$\underline{H}_2$" and substitute "CO$\underline{H}_2$".

Col. 10, line 67, delete "V" and substitute "$\bar{V}$".

Col. 11, line 54, delete "tert" and substitute "$\underline{tert}$".

Col. 11, line 62, delete "P" and substitute "$\underline{P}$".

Col. 11, line 65, delete "P" and "tert" and substitute "$\underline{P}$" and "$\underline{tert}$".

Col. 13, line 5, after "benzofuranyl(" delete "-".

Col. 13, line 18, after "m, OCH$_2$" delete "--".

Col. 13, line 38, delete "O-CH$_2$" and substitute "OCH$_2$".

UNITED STATES PATENT AND TRADEMARK OFFICE
CERTIFICATE OF CORRECTION

PATENT NO. : 4,394,383
DATED : July 19, 1983
INVENTOR(S) : M. Kawata et al

It is certified that error appears in the above-identified patent and that said Letters Patent are hereby corrected as shown below:

Col. 14, line 11, delete "CH$_2$)" and substitute "C$\underline{H}_2$)".

Col. 14, line 11, delete "CH$_3$)" and substitute "C$\underline{H}_3$)".

Col. 14, line 12, delete "OCH$_3$)" and substitute "OC$\underline{H}_3$".

Col. 16, line 32, delete "some" and substitute "same".

Col. 16, line 33, delete "LD$_{50}$ 50-105" and substitute "LD$_{50}$ 48-105".

Col. 17, line 14, delete "tert" and substitute "<u>tert</u>".

Col. 17, line 13, delete "n-butyl" and substitute "<u>n</u>-butyl".

Col. 17, line 15, delete "P" and substitute "<u>P</u>".

Col. 17, line 32, delete "carbamae" and substitute "carbamate".

Col. 18, line 4, delete "tert" and substitute "<u>tert</u>".

UNITED STATES PATENT AND TRADEMARK OFFICE
CERTIFICATE OF CORRECTION

PATENT NO. : 4,394,383                                        Page 3 of 3

DATED : July 19, 1983

INVENTOR(S) : M. Kawata et al

It is certified that error appears in the above–identified patent and that said Letters Patent are hereby corrected as shown below:

Col. 18, line 7, delete "P" and substitute "$\underline{P}$".

Col. 18, line 9, delete "P-tert" and substitute "$\underline{\text{P-tert}}$".

Signed and Sealed this

Twenty-ninth Day of January 1985

[SEAL]

*Attest:*

DONALD J. QUIGG

*Attesting Officer*        *Acting Commissioner of Patents and Trademarks*